(12) United States Patent
Eltorai et al.

(10) Patent No.: US 10,918,488 B2
(45) Date of Patent: Feb. 16, 2021

(54) INTERCARPAL SURGICAL IMPLANT

(71) Applicant: Orthopedix, Inc., Providence, RI (US)

(72) Inventors: Adam E. M. Eltorai, Providence, RI (US); Ashok Seetharam, Louisville, KY (US); Vishal Thomas, Louisville, KY (US)

(73) Assignee: Orthopedix, Inc., Louisville, KY (US)

( * ) Notice: Subject to any disclaimer, the term of this patent is extended or adjusted under 35 U.S.C. 154(b) by 0 days.

(21) Appl. No.: 15/602,501

(22) Filed: May 23, 2017

(65) Prior Publication Data

US 2018/0325674 A1   Nov. 15, 2018

Related U.S. Application Data

(60) Provisional application No. 62/505,954, filed on May 14, 2017.

(51) Int. Cl.
| | | |
|---|---|---|
| *A61F 2/42* | (2006.01) | |
| *A61F 2/30* | (2006.01) | |
| *G06F 30/20* | (2020.01) | |

(52) U.S. Cl.
CPC ........ *A61F 2/30942* (2013.01); *A61F 2/4261* (2013.01); *G06F 30/20* (2020.01); *A61F 2002/30772* (2013.01); *A61F 2002/30943* (2013.01); *A61F 2002/30948* (2013.01); *A61F 2002/30952* (2013.01); *A61F 2002/30962* (2013.01); *A61F 2002/30985* (2013.01); *A61F 2002/4287* (2013.01); *A61F 2002/4289* (2013.01); *A61F 2002/4292* (2013.01); *A61F 2002/4294* (2013.01)

(58) Field of Classification Search
CPC .. A61F 2/4261; A61F 2002/4264; A61F 2/30; A61F 2/42; A61F 2/4606; A61F 2002/4256; A61F 2002/4269; A61F 2/3094; A61F 2/30942
See application file for complete search history.

(56) References Cited

U.S. PATENT DOCUMENTS

| | | |
|---|---|---|
| 5,458,646 A | 10/1995 | Giachino et al. |
| 7,799,077 B2 | 9/2010 | Lang et al. |
| 7,918,894 B2 | 4/2011 | Wolfe et al. |
| 2006/0030946 A1 | 2/2006 | Ball et al. |

(Continued)

*Primary Examiner* — Ann Schillinger
(74) *Attorney, Agent, or Firm* — Armis IP Law, LLC

(57) ABSTRACT

A surgical implant for a proximal carpal row replacement surgery employs a scanned image of each of the scaphoid, lunate and triquetrum bones for generating a unitary, homogeneous model defining a fused shape for implantation as the proximal carpal row. The implant utilizes a contralateral image of healthy bones of the patient for generating the replacement model, and employs shrink-wrap and smoothing processing to generate the unitary replacement. The resulting implant replaces the intercalary bone structures of the scaphoid, lunate and triquetrum with a single appliance, and is slideably engaged with the distal carpal row via a surgical tunnel and tethered by a resectioned tendon, ligament, or other connective member. The implant facilitates wrist function since the unitary implant replaces skeletal structures that are encapsulated by adjacent bones and frequently move as a unit, while eliminating gaps, voids and ligaments between the intercalary structure.

8 Claims, 4 Drawing Sheets

(56) References Cited

U.S. PATENT DOCUMENTS

| | | | |
|---|---|---|---|
| 2011/0295378 A1* | 12/2011 | Bojarski | A61F 2/30942 623/20.35 |
| 2014/0058524 A1* | 2/2014 | Gray | A61F 2/2846 623/20.17 |
| 2015/0032215 A1* | 1/2015 | Slamin | A61F 2/389 623/20.21 |
| 2019/0076262 A1* | 3/2019 | Eltorai | A61F 2/4261 |
| 2019/0201207 A1* | 7/2019 | Giusti | A61F 2/0811 |

* cited by examiner

INTERCARPAL SURGICAL IMPLANT

RELATED APPLICATIONS

This application claims the benefit under 35 U.S.C. § 119(e) of U.S. Provisional Patent Application No. 62/505,954 filed May 14, 2017, entitled "CUSTOM INTER-CARPAL SURGICAL IMPLANT," incorporated herein by reference in entirety.

BACKGROUND

Prosthetic appliances are surgical implants that replace natural skeletal structures in a patient. Natural skeletal structures such as bones, tendons and ligaments can be compromised by age, disease and traumatic injury, as well as other causes. Surgical replacement with an orthopedic implant attempts to duplicate the original bone or skeletal member so that the patient may continue to enjoy mobility and dexterity once provided by healthy skeletal members. Replacement orthopedic implants are particularly beneficial in the wrist, as the natural skeletal structures include an arrangement of small, interconnected bones having specific irregular shapes that mesh and cooperate with other adjacent bones. Modern developments in CAD/CAM (computer aided design/computer aided manufacturing) has facilitated fabrication of these complex shapes.

Since the wrist is not a single-axis joint with collateral ligaments guiding a unidirectional arc of motion, the unconstrained wrist seldom rotates in a pure flexion-extension or radial-ulnar deviation mode, due to multiple degrees of freedom. In fact, most activities of daily living (using a hammer, fishing, bouncing a ball, or lifting heavy objects) involve an oblique type of wrist motion, from extension-radial deviation to flexion-ulnar deviation; it is the so-called "dart-throwing" plane of motion.

The human wrist helps to place the hand in optimal positions to perform a variety of tasks. For this reason, it is vital for hand function. When the wrist is degraded by disease or injury, hand function is compromised. As the wrist is a complex collection of multiple articulations, its anatomy and function is also complex.

SUMMARY

A surgical implant for a proximal carpal row replacement surgery employs a scanned image of each of the scaphoid, lunate and triquetrum bones for generating a unitary, homogeneous model defining a fused shape for implantation as the proximal carpal row. The implant utilizes a contralateral image of healthy bones of the patient for generating the replacement model, and employs shrink-wrap and smoothing processing to generate the unitary replacement. The resulting implant replaces the intercalary bone structures of the scaphoid, lunate and triquetrum with a single appliance, and is slideably engaged with the distal carpal row via a surgical tunnel and tethered by a resectioned tendon, ligament, or other connective member. The implant facilitates wrist function since the unitary implant replaces skeletal structures that are encapsulated by adjacent bones and frequently move as a unit, while eliminating gaps, voids and ligaments between the intercalary structure.

Configurations herein are based, in part, on the observation that human skeletal wrist structures employ a complex arrangement of skeletal structures including bones, ligaments and tendons that interoperate for distributing forces over a wide range of possible wrist articulations. Unfortunately, conventional approaches for orthopedic implant replacement suffer from the shortcoming that a plurality of small bones and connective tissue present complexities when developing suitable replacement implants. Rigid inter-skeletal connections such as pins and screws are often used that fix bones in positions that may limit movement. Complex surfaces and force distribution involved in wrist manipulation can result in a surgical implant falling short of providing support for movement capabilities of the natural skeletal structures it replaces.

Accordingly, configurations herein substantially overcome the shortcomings of fixed or imprecise implants by teaching an implant based on a combination or fusing of adjacent bones to define a unitary, homogeneous surgical implant that eliminates unneeded or redundant inter-bone structures in an intercalary structure that moves and reacts as a single unit. In an example configuration discussed herein, the proximal carpal row (PCR) bones are bound together with very strong ligaments and act as a single row in most instances. It is also an intercalary segment, that is, it has no muscle/tendon attachment directly to it. The forces and thereby the control of the proximal carpal row is therefore indirect through the tendon insertions in the distal carpal row and beyond.

The implant employs contralateral imaging for including features based on a native bone structure and shape, and by eliminating ligaments that bind a group of sequential bones, removes problematic connective tissue while maintaining a substantially similar function of bones that frequently act as a single collective structure.

In further detail, the disclosed method of fabricating and implanting a surgical appliance includes receiving a scanned image of a plurality of adjacent skeletal structures designated for replacement, and also receiving a contralateral scan of the skeletal structures designated for replacement. A modeling processor generates, based on the scanned image and an inversion of the contralateral scan, a model of an implant corresponding to each of the adjacent skeletal structures, and combines the models of each of the adjacent skeletal structures into a unitary, homogeneous model adapted for 3D printing for generating a surgical implant configured for replacement of the adjacent skeletal structures. During fabrication, the modeling processor or fabrication system compares the scanned image to the contralateral scan and a healthy image depicting an uncompromised skeletal structure, and generates the models based on the scanned image and the healthy image.

Orthopedic wrist implants are expected to benefit a diverse array of customers. First and foremost, patients suffering from thumb CMC arthritis, Kienbock's disease and scaphoid non-union fracture, none of which enjoy proven and long lasting treatments, can have a anatomically accurate replacement of the damaged bone designed specifically for them. Such conformity translates to a better perceived fit, shorter recovery time and improved osteo-integration. Surgeons benefit in the way of reduced infection risks and higher satisfaction among their patients. Providers have the benefit of reduced inventory costs, higher throughput and implants on demand based on individual, patient-specific fabrication.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example of a surgical implant fabrication and corresponding implantation procedure that fabricates the unitary model of a plurality of intercalary bone structures such as in a proximal carpal row of a wrist, and describes a procedure for surgical implantation including non-rigid attachment to adjacent structures that avoids the need for pins or screws to secure bone-to-bone attachments. Complex bone structures that permit multiple degrees of freedom, such as in the ankle and wrist regions, often employ varied positional and soft tissue connections to proximate and adjacent skeletal structures. Some bones may move relatively little relative to adjacent bones, and may be secured merely by a positional surrounding of the adjacent bones, a so-called intercalary structure having no tendinous linkages. An example of a wrist implant is disclosed below, for replacing the three bones in the proximate carpal row, however the disclosed approach may be applied to other sequences of adjacent, positionally secured bones.

Figure 1:
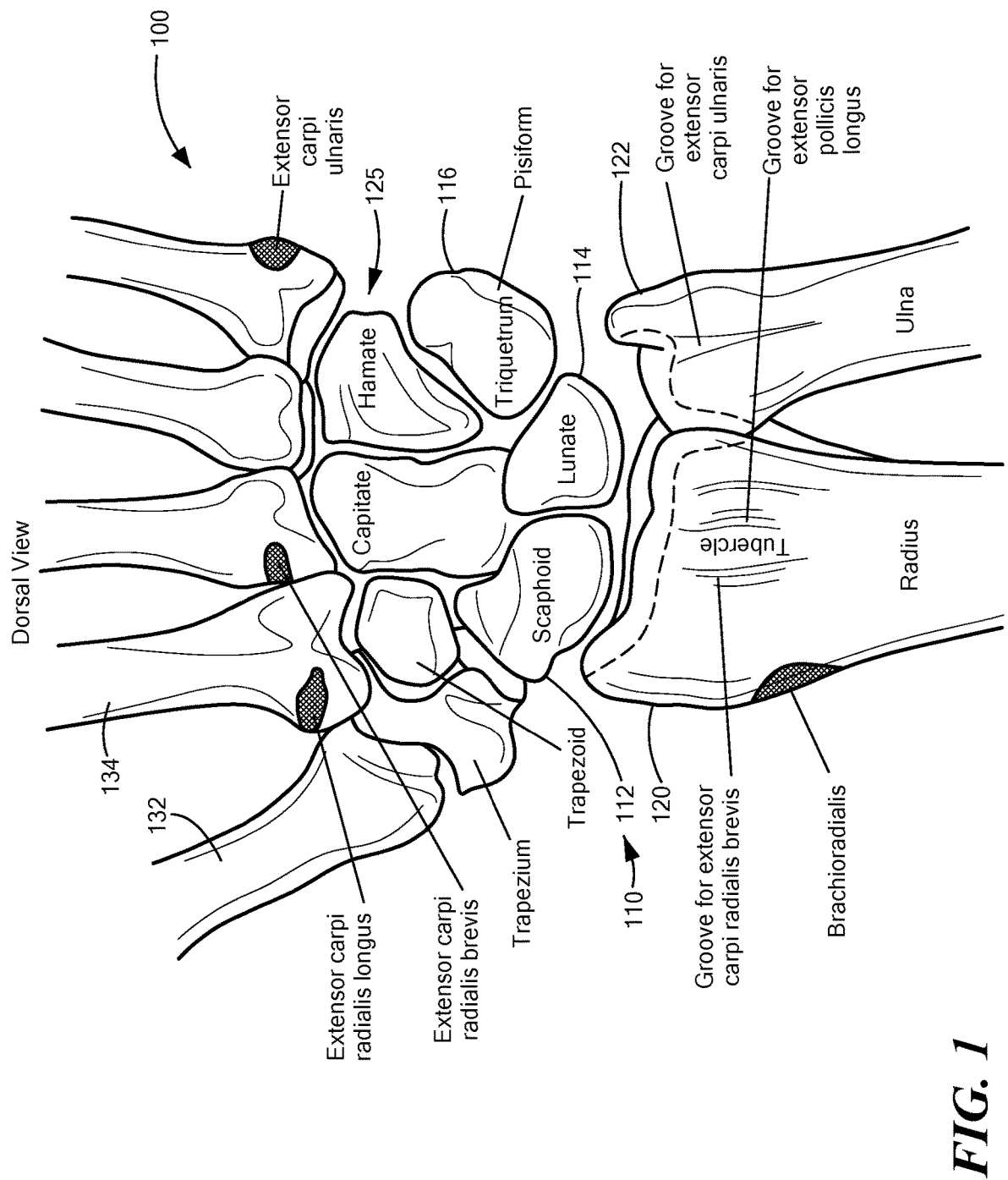
FIG. 1 is an anatomical diagram of a wrist suitable for depicting usage of the approach disclosed herein.

FIG. 1 is an anatomical diagram of a wrist suitable for depicting usage of the approach disclosed herein. Referring to FIG. 1, in a patient wrist 100 includes a proximal carpal row (PCR) 110 defined by three adjacent bones: the scaphoid 112, lunate 114 and triquetrum 116. The proximal carpal row 110 resides adjacent the distal radius 120 and ulna 122, and abuts the distal carpal row 125 on a side nearest the digits (fingers). A second metacarpal 134 is adjacent the thumb, or first metacarpal 132, and will be discussed further below. As can be seen in the dorsal (opposite of palm side) wrist view of FIG. 1, the scaphoid 112, lunate 114 and triquetrum 116 are tightly disposed in position between the radius 120/ulna 122 at the end of the arm on one side and the distal carpal row 125 on the opposed side nearest the fingers. These adjacent bones "fit" almost as if pieces of a jigsaw puzzle, held in place by surrounding bones and other soft tissue such as ligaments and muscles. In various configurations, the disclosed approach is operable for use with adjacent skeletal structures that are intercalary bone structures secured by proximate, disconnected skeletal structures.

Figure 2:
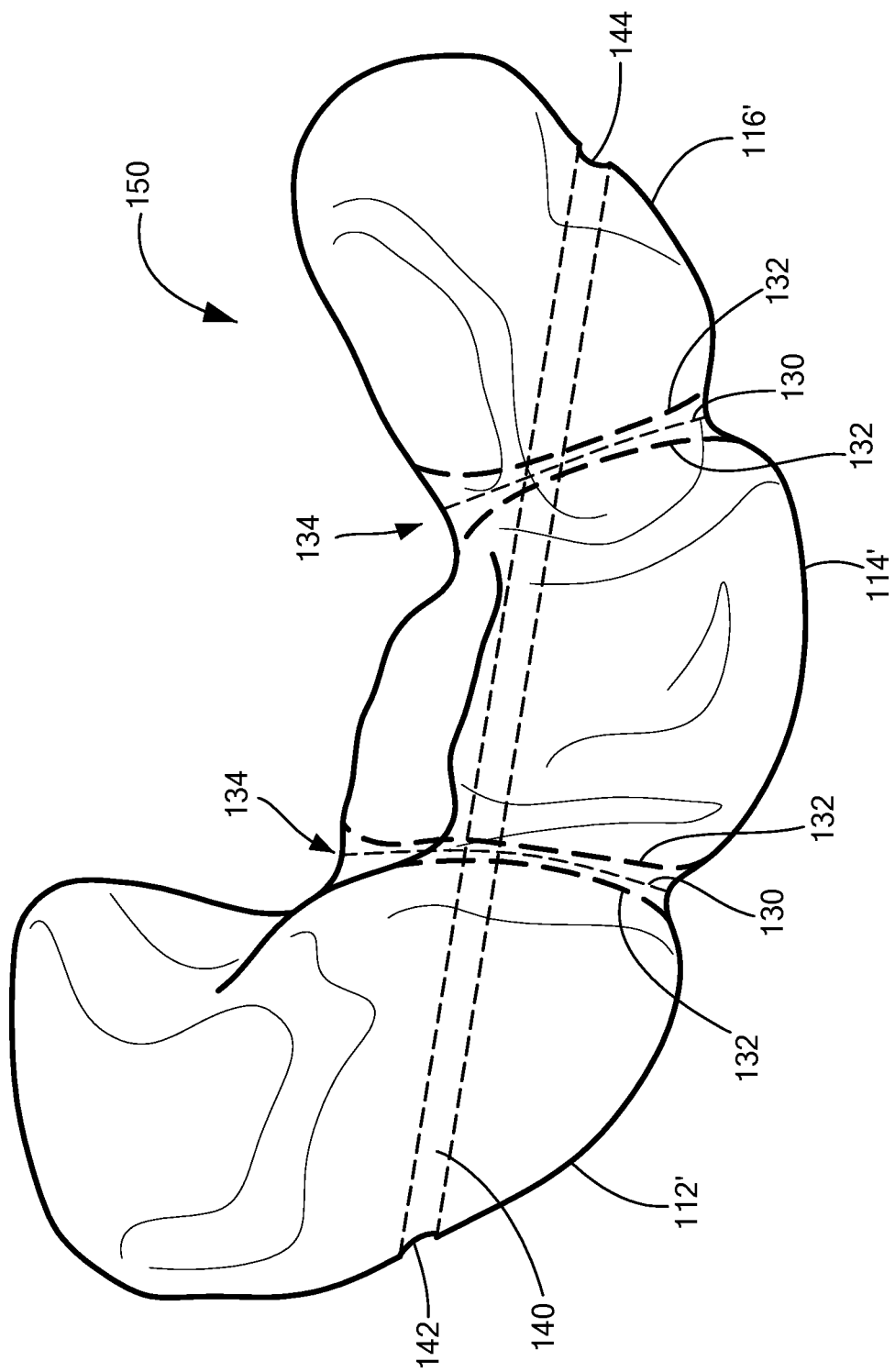
FIG. 2 is a perspective view of an implant suitable for use in the anatomical region of FIG. 1.

FIG. 2 is a perspective view of an implant model 150 suitable for use in the anatomical region of FIG. 1. Referring to FIGS. 1 and 2, the surgical implant 150 has portions derived from the scaphoid 112', lunate 114' and triquetrum 116'. Each of the adjacent bone portions is delineated by fine dotted lines 130, and the actual bone dimensions approximated by course dotted lines 132. The fusing, or aggregation area 134 is established by shrink-wrap processing and smoothing processing that purports to align and merge different orientations of surface and planar shapes. The fused model results from adjacent skeletal structures formed as a single unit by combining, smoothing and filling a model of each of the adjacent skeletal structures by augmenting voids between adjacent surfaces to approximate a surface defined by the outwardmost points on the exterior of each of the adjacent bones which the void divides. The model 150 therefore defines a proximal carpal row 110 and the unitary, homogeneous model is a fused shape for implantation as a scaphoid 112, lunate 114 and triquetrum 116. A surgical tunnel 140 extends through the implant 150 between orifices 142 and 144 for insertion of a tether or attachment member, such as a suture or tendon, also discussed further below. In this manner, the surgical implant is adapted for implantation and engagement with the flanking skeletal structures.

The surgical implant is rendered from a 3-D (3 Dimensional) rendering platform, typically a 3-D printer or additive manufacturing techniques, based on the model resulting from scans of the bones 112, 114 and 116 and combination of the model into the fused shape of the implant. Contralateral imaging to approximate the natural shape based on the bone structure of the opposed wrist of the same patient ensures an accurate implant. Such imaging and fabrication may be as disclosed in copending U.S. patent application Ser. No. 15/412,458, filed Jan. 23, 2017, entitled "CONTRALATERAL IMAGE ORTHOPEDIC IMPLANT," incorporated herein by reference in entirety. By using contralateral images of the patient's own anatomy of the adjacent bones, the single implantable body device has anatomical features of each of the replaced adjacent skeletal structures. Contralateral imaging is beneficial for features common to both sides (right and left) of a patient because they tend to share similar but in a reversed, or inverted arrangement.

Figure 3:
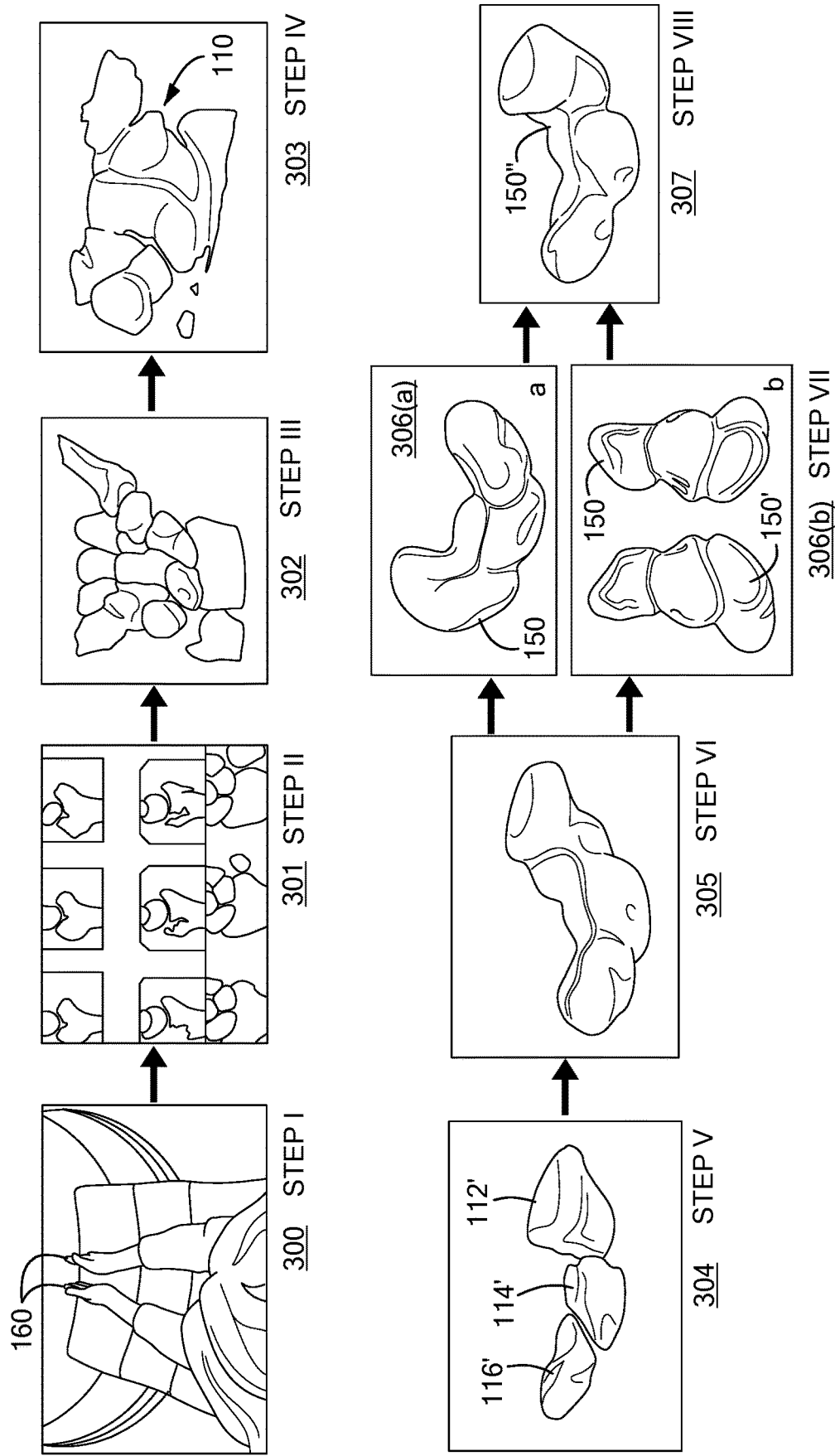
FIG. 3 is a stepwise progression of implant fabrication for generating the implant in FIG. 2.

FIG. 3 is a stepwise progression of implant fabrication for generating the implant in FIG. 2. Referring to FIG. 1-3, at step 300, a scan of bilateral forearm 160 of the patient is taken. Any suitable scan may be employed, such as Computerized Axial Tomography (CT or CAT) scan or Magnetic Resonance Imaging (MRI). This CT scanning protocol consists of a localizer and a detailed axial scan of the (bilateral) forearm. The CT scan quality (with clear bony edges and details) is beneficial to the production of an accurate patient-specific implant, and can usually be accomplished with a single acquisition.

The CT scan are post processed to create DICOM (Digital Imaging and Communications in Medicine) or other modeling format files, as disclosed at step 301. These DICOM files will serve as a basis for 3D modeling of the implant. The 2D scan DICOM files are processed to create 3D representations of the patient's anatomy, as depicted at step 302, and segmentation of reconstructed 3D model performed at step 303. Segmentation of the desired region (carpal bones) may be performed, for example, using a segmentation toolbox in the MIMICS® software suite. In the disclosed approach, the 3D files are represented in the STL format, from the DICOM input format, however other image formats such as: TIFF, JPEG, BMP and Raw may be employed. Output file formats differ, depending on the subsequent application; common 3D output formats include STL, VRML, PLY and DXF.

From the segmented 3D files, the approach performs identification and segmentation of the PCR bones: scaphoid 112, lunate 114 and, triquetrum 116, as disclosed at step 304. Each of these bones are identified and segmented for 3D measurements which leads to anatomical landmark points of the optimal designing of the replacement. Segmentation identifies volumetric, surface and landmark features for duplicating the anatomy of the scanned skeletal member. The result is the surface characteristics and features indicative of the anatomy, and thus captures the physical features such that the fused structure will be accommodated between the distal carpal row 125 and the radius/ulna 120, 122.

From step 304, depicting models of each of the constituent bones, Proximal Carpal row (PCR) replacement is designed using image processing techniques such as shrinkwrap and smoothing filter processing. This involves forming the fused shape by applying a circumferential contour processing technique and a smoothing filter to the generated models 112', 114' 116' of the adjacent skeletal structures. The resulting model is a combined single body device with the anatomy of all three PCR bones, as shown at step 305. In the example configuration, the one-piece PCR replacement will have a central 3 mm diameter hole running form the radial scaphoid side at orifice 142 to the ulnar triquetrum side at orifice 144. Since the proximal row is an intercalary segment, the PCR replacement need not be implanted into any bone, nor rigidly attached to any structure. This feature removes the need for intra-medullary fixation and osseointegration of the implant.

As indicated above, the contralateral imaging is employed to obtain a healthy representation of a mirror image bone, which may then be inverted to generate a substantially similar bone having features of the patient's own anatomy. In the case where the contralateral side is also compromised, an ideal "healthy" bone model is employed and combined with the contralateral scan to mitigate deviant features of the contralateral scan. Referring to step 306(*a*), In case of bilateral disease or use of the same side anatomy, the same side scan may be employed as the model for 3D printing.

Preferably, however, the healthy side wrist of the patient is employed, such that the resulting PCR replacement design 150' is then converted into a mirror image 150 to match the anatomy of the diseased wrist, as depicted at step 306(*b*).

The implant design file is then converted into an .stl (stereolithography) file and is then uploaded on the printer with desired print medium material. Any suitable biocompatible medium may be employed, such as PEEK/PEAK/PMMA/UHWMPE/graphite polymer/pyrolytic carbon, to render/print the replacement. In a particular configuration, a cobalt chromium alloy may be employed as the print medium. Any suitable print medium, however, may be employed for rendering the fabricated surgical implant 150". The completed implant 150" is a fabricated unitary, homogeneous surgical implant 150" based on an inverted, contralateral scan of a sequence of adjacent skeletal structures formed as a single unit by combining, smoothing and filling a model of each of the adjacent skeletal structures, as disclosed above.

Figure 4:
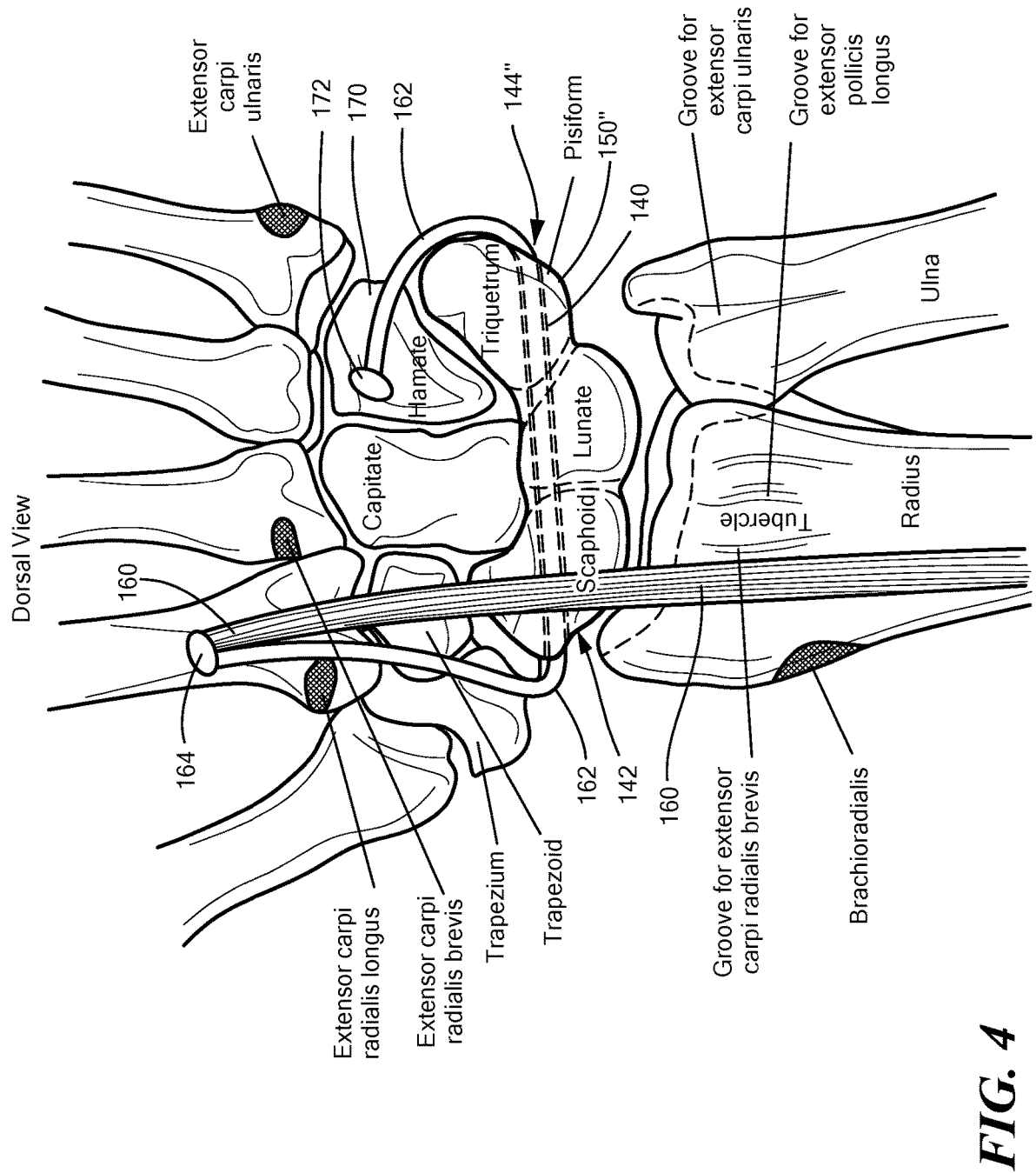
FIG. 4 shows the fabricated implant after surgical implantation.

FIG. 4 shows the fabricated implant after surgical implantation. A tunnel 140 is formed through the generated surgical implant 150", and extends from a radial scaphoid side to the ulnar triquetrum side. Referring to FIGS. 1, 2 and 4, the implant 150" includes the surgical tunnel 150 formed either from omission of print medium during the rendering process or drilling the finished implant 150". The tunnel 140 is adapted for securement by slideable engagement through an orifice 142, 144 in the surgical implant 150" with a tethered attachment to one or more of the proximate skeletal structures.

The surgical implant is expected to be securely engaged by the adjacent skeletal structures, due to the complex wrist anatomy. Alternatively, the implant 150" may benefit from additional attachment or tethering. Surgical implantation may therefore involve forming a tethering attachment to the fabricated surgical implant, and attaching a tethering element between the tethering attachment and a proximate skeletal structure for slideably engaging the installed surgical implant with the tether. The tethering attachment is a surgical tunnel 140 extending between orifices 142, 144 in an external surface of the surgical implant for receiving a tethering element, such that the tethering element remains in an unfixed position on the surgical implant for slideable communication therewith. In other words, the implant 150" is not fixedly attached to the tethering element, but rather may slide along the tether as wrist movement directs. The implantation secures each of the ends of the tethering elements (typically a suture or tendon) to a respective fixation point on a proximate skeletal member.

In the disclosed approach, native tissue may be employed as the tethering element. During implantation, a native connecting member adjacent to the surgical implant is harvested by bifurcating an existing structure. The harvested connecting member is disposed through the surgical tunnel 140 to define the tethering element, and the remaining end of the connecting member 162 is attached to a proximate skeletal member.

For the PCR application, this process is particularly beneficial because the native PCR has no tendon insertions. Wrist motor tendons are inserted onto the distal row or at the base of the metacarpals. While the pisiform has a tendon insertion, it is not a true proximal row bone, but rather a sesamoid to enhance the mechanical advantage of the FCU. Consequently, when one of these muscles contract only the distal row starts moving. The proximal row does not rotate until a certain level of tension develops in the midcarpal crossing ligaments; that tension generates eccentric compressive forces in the midcarpal joint forcing the proximal bones to move. Since the proximal row is an intercalary segment, the PCR replacement does not have to be implanted into any bone. This relieves the need for intramedullary fixation and osseointegration of the implant.

The geometry of the PCR replacement will give intrinsic stability as it will match the patient's normal proximal row. The scaphoid and lunate will fit into the scaphoid and lunate fossa of the radius and the distal carpal row will fit nicely in the distal position of the PCR replacement and transmit forces to it. The volar radiocarpal ligaments will be largely untouched and therefore will provide volar stability. Dorsally, implantation involves detaching the dorsal intercarpal ligament (DIL) and the dorsal radiocarpal ligament (DRCL) from their attachment to the triquetrum for redirection radially to facilitate the excision of the lunate and triquetrum. Once the PCR implant is in place, the DIL and DRCL are transferred to the dorsal hamate with a suture anchor thereby providing dorsal stability. The surgical tunnel 140 in the one piece PCR replacement is a central 3 mm diameter hole running form the radial scaphoid side to the ulnar triquetrum side. The tunnel 140 is adapted to receive a bifurcated flexor carpi radialis tendon for passage through the tunnel and attachment to a proximate skeletal structure.

Configurations herein harvest a third of the flexor carpi radialis (FCR) tendon, leave it attached distally to the base of the 2nd metacarpal, pass it through the central hole in the PCR replacement implant 150" and attach it dorsally to the hamate on the ulnar side and the point of DIL and DRCL attachment. This will keep the PCR replacement implant 150" firmly attached to the distal carpal row 125, thus enhancing stability.

The implant 150", in replacing the PCR 110, may therefore include securing the surgical implant 150" by slideable engagement through an orifice 142 in the surgical implant 152" with a tethered attachment to one or more of the proximate skeletal structures, such as the distal carpal row 125. The flexor carpi radialis is a tendon running adjacent to the PCR that may be utilized for such slideable engagement. A portion 162 of the flexor carpi radialis (FCR) tendon 160 is bifurcated or excised, by leaving it attached distally to the base 164 of the 2nd metacarpal, and passing through the orifice 142 and tunnel 140 in the PCR replacement. The tendon portion 162 slideably tethers the implant 150", rather than attaching directly and/or fixing the implant to either the distal carpal row 125 or the radius 120/ulna 122.

Those skilled in the art should readily appreciate that the programs and methods defined herein are deliverable to a user processing and rendering device in many forms, including but not limited to a) information permanently stored on non-writeable storage media such as ROM devices, b) information alterably stored on writable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method of fabricating a surgical implant, comprising:
    receiving a scanned image of a plurality of adjacent skeletal structures designated for replacement, the plurality of adjacent skeletal structures defining a proximal carpal row (PCR) including an ordered arrangement of a scaphoid, lunate and triquetrum;
    receiving a contralateral scan of each of the adjacent skeletal structures designated for replacement;
    comparing the scanned image of each of the adjacent skeletal structures of the plurality of skeletal structures to the respective contralateral scan and a healthy image depicting an uncompromised skeletal structure of the respective skeletal structure;
    generating, based on the scanned image, the healthy image and an inversion of the contralateral scan of each of the adjacent skeletal structures, a model of an implant corresponding to each of the adjacent skeletal structures;
    fusing the models of each of the adjacent skeletal structures into a unitary, homogeneous model defined by a continuous combined shape based on an aggregation area between the adjacent skeletal structures resulting from a smoothing of the surfaces and planar shapes of the adjacent skeletal structures, the unitary, homogeneous model for implantation as replacement to the scaphoid, lunate and triquetrum and adapted for 3D printing for rendering the surgical implant configured for replacement of the adjacent skeletal structures; and
    forming a surgical tunnel through the surgical implant for insertion of a surgical tether therethrough, the surgical tunnel extending linearly from an opening on a radial scaphoid side and longitudinally extending to an opening on an ulnar triquetrum side.

2. The method of claim 1 wherein the surgical implant is adapted for implantation and engagement with the adjacent skeletal structures.

3. The method of claim 2 wherein the surgical implant has anatomical features of each of the replaced adjacent skeletal structures.

4. The method of claim 1 wherein the surgical implant is adapted for securement by slideable engagement through an orifice in communication with the surgical tunnel in the surgical implant with the surgical tether for forming a tethered attachment to one or more of the proximate skeletal structures.

5. The method of claim 4 wherein the surgical tunnel is adapted to receive a bifurcated flexor carpi radialis tendon for passage through the tunnel and attachment to a proximate skeletal structure.

6. The method of claim 1 further comprising forming the unitary, homogeneous model by applying a circumferential contour processing technique and a smoothing filter to the generated models of each of the adjacent skeletal structures.

7. The method of claim 1 further comprising comparing the scanned image of each of the adjacent skeletal structures to an inversion of a contralateral scan of the corresponding skeletal structure of an opposed wrist, and
    selecting anatomical features of one of the contralateral scan and healthy image for the model of the implant for each of the skeletal structures.

8. The method of claim 7 further comprising
    forming the unitary, homogeneous model by filling surface areas in adjacent skeletal structures by an aggregation zone defined by an augmented void between the adjacent skeletal structures, the augmented void based on an outward most points forming a smoothed perimeter around the unitary, homogeneous model.

* * * * *